US00PP15423P2

(12) United States Plant Patent
Schlueter

(10) Patent No.: US PP15,423 P2
(45) Date of Patent: Dec. 14, 2004

(54) ***HIBISCUS ROSA-SINENSIS* PLANT NAMED 'HEARTBEAT'**

(50) Latin Name: *Hibiscus rosa-sinensis*
Varietal Denomination: Heartbeat

(75) Inventor: Barry Schlueter, Houston, TX (US)

(73) Assignee: Hines Nurseries, Inc., Irvine, CA (US)

( * ) Notice: Subject to any disclaimer, the term of this patent is extended or adjusted under 35 U.S.C. 154(b) by 54 days.

(21) Appl. No.: 10/764,060

(22) Filed: Jan. 23, 2004

(51) Int. Cl.[7] ..... A01H 5/00
(52) U.S. Cl. ..... Plt./257
(58) Field of Search ..... Plt./257

*Primary Examiner*—Kent Bell
(74) *Attorney, Agent, or Firm*—Christie, Parker & Hale, LLP

(57) ABSTRACT

A new plant variety of *Hibiscus rosa-sinensis,* named 'Heartbeat', characterized by a large glowing dark pink to light red flower with exceptional symmetry. It is a free-flowering plant with an upright, compact habit. The foliage is glossy and dark green.

4 Drawing Sheets

Botanical classification: *Hibiscus rosa-sinensis* L.
Varietal denomination: The new plant has the varietal denomination 'HEARTBEAT'.

BACKGROUND OF THE INVENTION

The present invention relates to a new and distinct variety of *Hibiscus rosa-sinensis* L., which was developed in a controlled breeding program in Webster, Tex.

The genus *Hibiscus* comprises about 250 species of herbs, shrubs and trees in warm temperature and tropical regions; with leaves usually simple, mostly palmately veined, lobed or parted; flowers mostly solitary in the leaf axils but sometimes in racemes, corymbs or panicles. *Hibiscus* is included in the family Malvaceae, which comprises about 95 genera of herbs, shrubs and trees originating in tropical and temperature regions. *Hibiscus rosa-sinensis* is a glabrate shrub, seldom over 8 feet tall in cultivation, but treelike to 15 feet or more in tropical regions. Leaves to 6-inches long, ovate, usually serrate, mostly glossy green. Flowers solitary in upper leaf axils.

The new *Hibiscus* is a product of a planned breeding program conducted by the inventor in Webster, Tex. The objective of the program was to create new *Hibiscus* selections with improved bloom quality, color and floriferousness, plants that can be commercially produced on their own root systems, and improved plant habit with regard to vigor and postproduction longevity.

The new *Hibiscus* originated from a cross-pollination made by the Inventor using 'Miss Liberty' (not patented) as the female parent and 'Burnished Gold' (not patented) as the male parent. The new *Hibiscus* was discovered and selected by the Inventor as a plant within the progeny of the stated cross-pollination in a controlled breeding program in Webster, Tex.

SUMMARY OF THE INVENTION

The new variety was discovered in a controlled breeding program of *Hibiscus rosa-sinensis* and differs from its parents and other known cultivars of *Hibiscus rosa-sinensis* by the following characteristics in combination:

1. Upright, compact symmetrical plant habit that is suitable for container production;
2. Healthy green foliage;
3. Vigorous growth habit;
4. Large dark pink to light red flowers with perfect symmetry and depth of color;
5. Free-flowering.

Asexual reproduction of the new variety by stem cuttings, performed in Webster, Tex. and Fulshear, Tex. have confirmed that the distinctive characteristics of the new variety are stable and transmitted to succeeding generations, and the new variety reproduces true to type.

COMPARISON WITH PARENTS AND OTHER CULTIVARS

'Heartbeat' is distinguished from its female parent 'Miss Liberty' (not patented) by having a more consistent flower color throughout than the pink blend of 'Miss Liberty'; also, 'Heartbeat' had a dark eye compared to the white eye of 'Miss Liberty'. 'Heartbeat' is also a strong, upright, well-branched plant with more disease resistant foliage than 'Miss Liberty'. 'Heartbeat' is distinguished from its male parent 'Burnished Gold' (not patented) by its flower color; flowers of 'Burnished Gold' are a mixture of gold and reddish brown with a smooth surface and no tufting.

Plants of 'Heartbeat' can be compared to plants of the cultivar 'Vulcan' (not patented). However, in side-by-side comparisons conducted in Webster, Tex., plants of 'Heartbeat' differ from plants of the cultivar 'Vulcan' in the following characteristics:

1. Flowers of 'Heartbeat' are brighter in color than flowers of 'Vulcan';
2. Plants of 'Heartbeat' are easier to propagate via vegetative cuttings than plants of the cultivar 'Vulcan';

BRIEF DESCRIPTION OF ILLUSTRATIONS

The accompanying illustrations show a specimen of the new cultivar in a photographic illustration as true to color as is reasonably possible to make in an illustration of this character.

DETAILED DESCRIPTION OF THE NEW VARIETY

Figure 1:
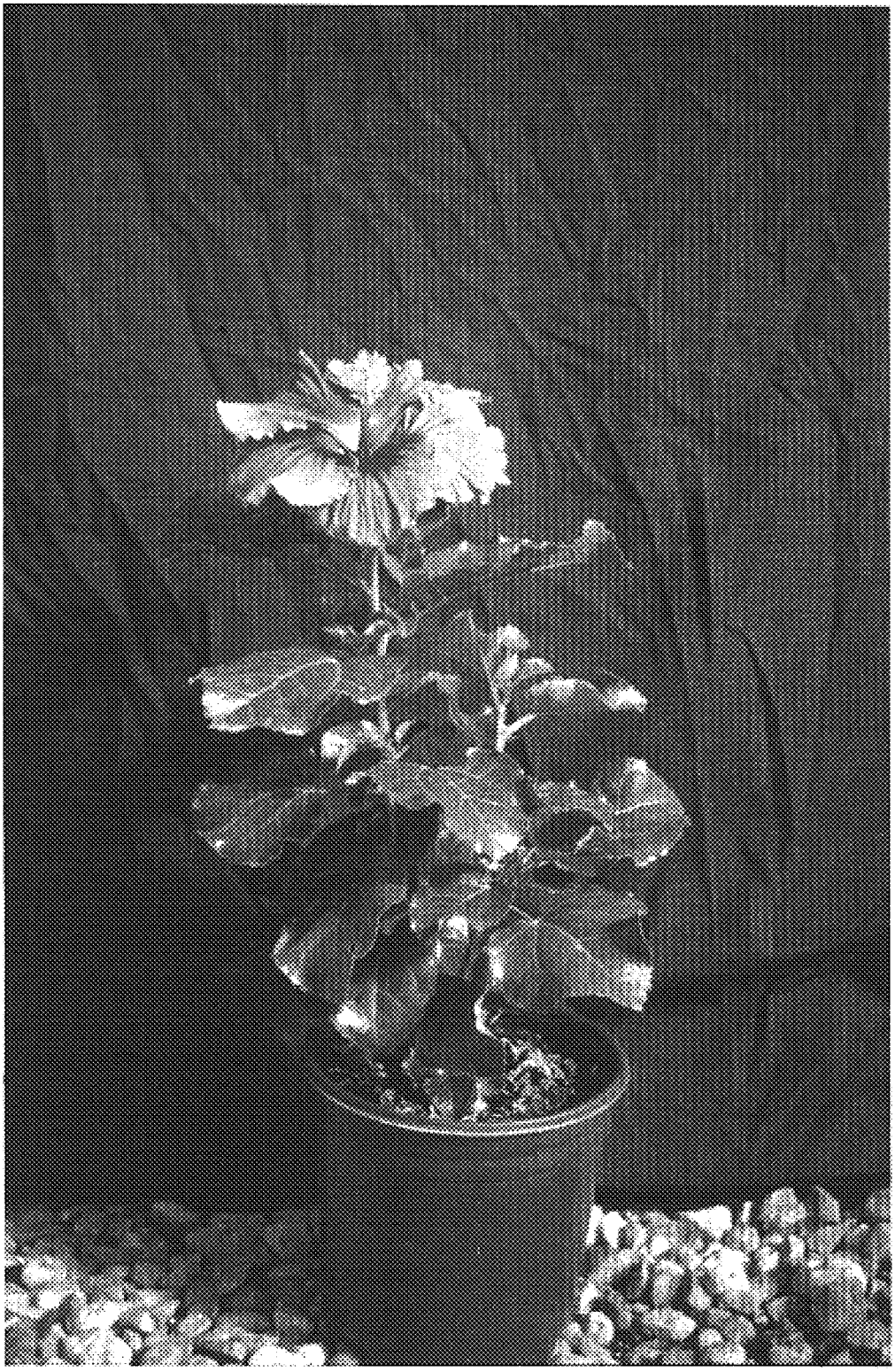
FIG. 1 illustrates a side perspective view of a typical plant of 'Heartbeat'.
Figure 2:
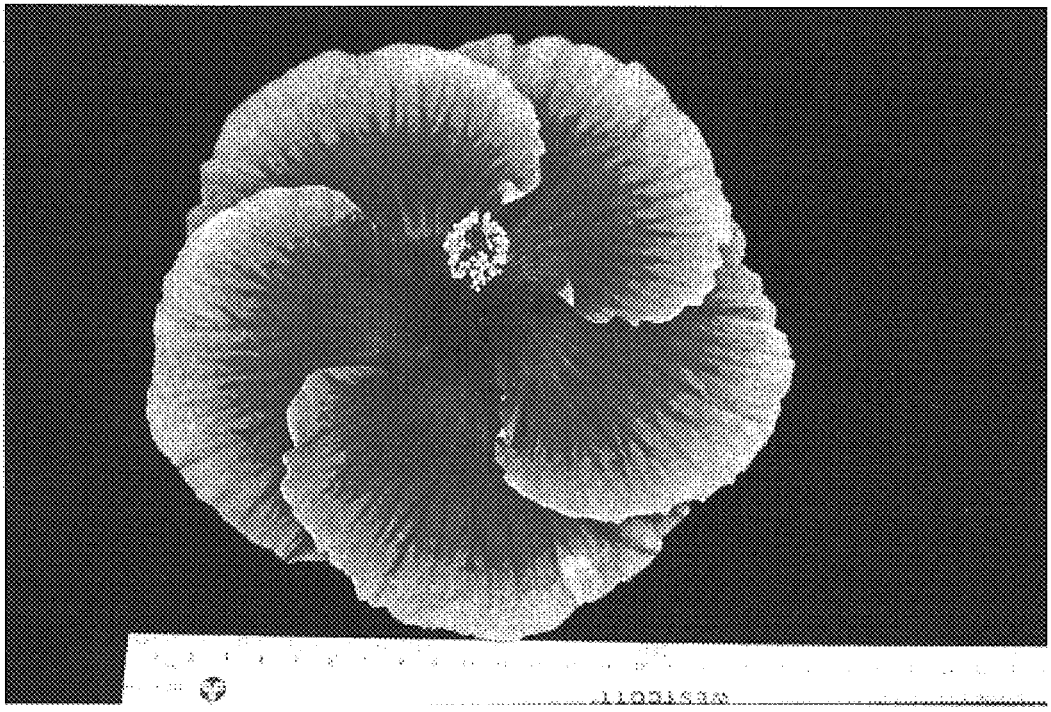
FIG. 2 illustrates the scale of a typical flower of 'Heartbeat'.
Figure 3:
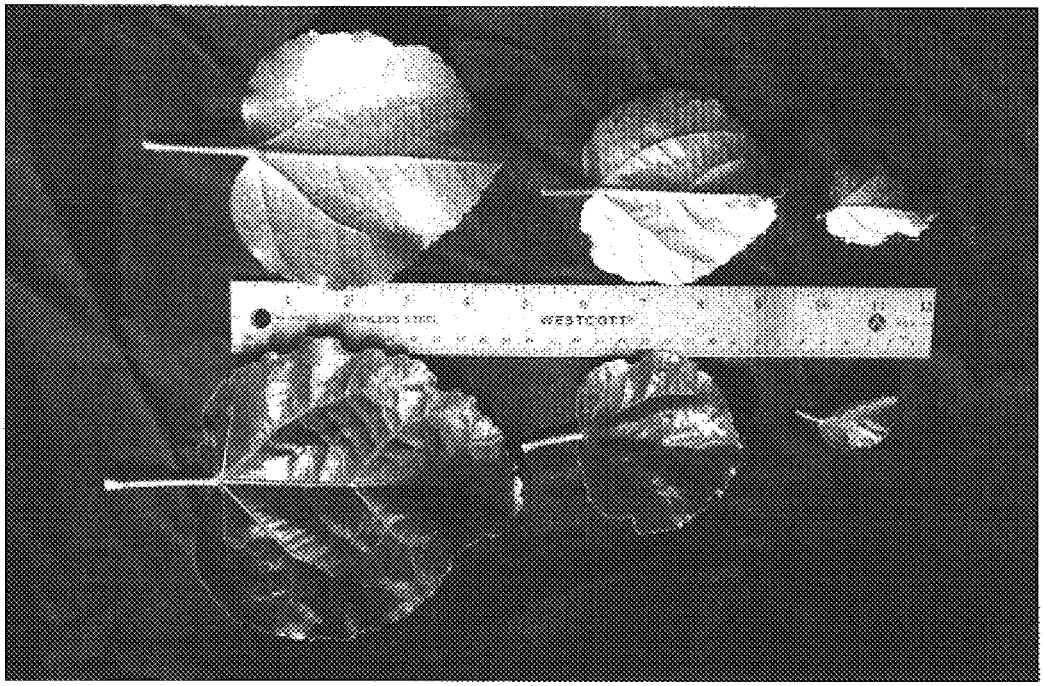
FIG. 3 illustrates the typical young to mature foliage of 'Heartbeat'; the abaxial and adaxial surfaces are shown at each stage.
Figure 4:
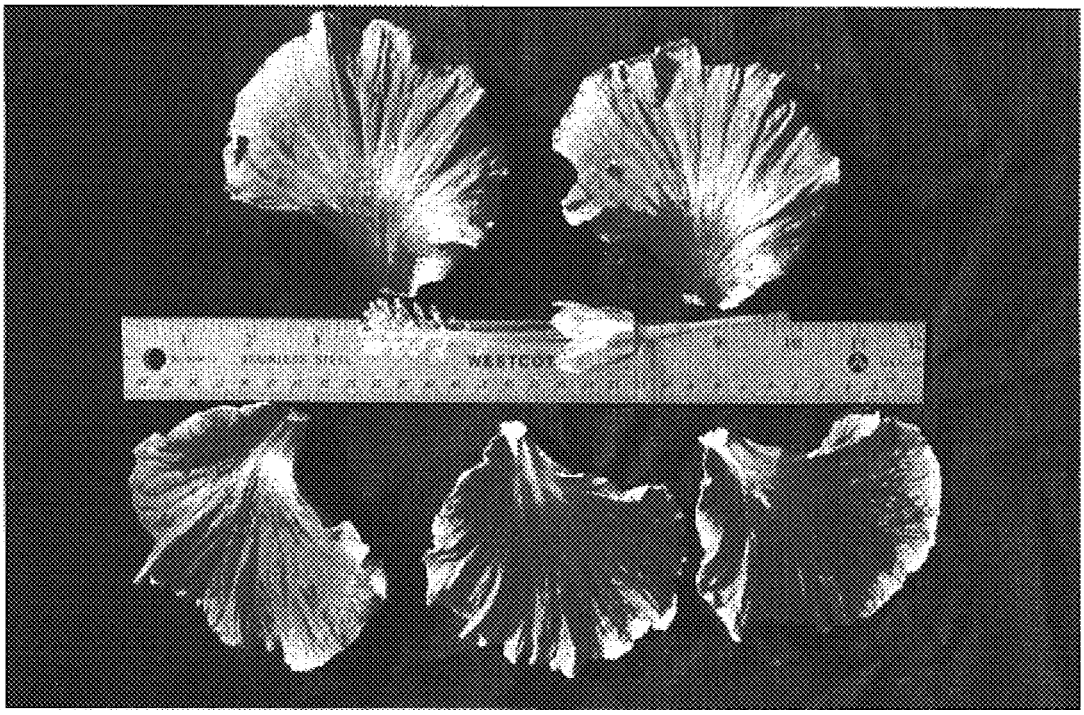
FIG. 4 illustrates a dissected flower of 'Heartbeat', including shape and size of petals and characteristics of the reproductive structures.

'Heartbeat' has not been observed under all possible environmental, cultural and light conditions. The following observations and descriptions are of plants grown in Fulshear, Tex., in February 2003, under polypropylene shadecloth providing a 30 percent light reduction, and under conditions which closely approximate commercial production. Plants described were approximately one year old and in a #3 nursery container. In this description, color references are to The Royal Horticultural Society Colour Chart (2000) and terminology used in the color descriptions herein refers to plate numbers in this color chart. Phenotypic expression may vary with light intensity, cultural and environmental conditions.

Classification:

*Botanical.*—*Hibiscus rosa-sinensis* L. 'Heartbeat'.

*Parentage.*—Female or Seed Parent: *Hibiscus rosa-sinensis* 'Miss Liberty' (not patented). Male or Pollen Parent: *Hibiscus rosa-sinensis* 'Burnished Gold' (not patented).

*Propagation.*—By stem cuttings.

*Time to initiate rooting.*—Approximately 14 to 21 days at 21–24 C.

*Time to develop roots.*—Approximately 42 to 56 days at 21–24 C.

*Root description.*—Fine to medium; fibrous; freely branching.

Plant:

*Size.*—Height: Approximately 51 cm from soil level to top of flowers. Diameter/Spread: Approximately 60 cm.

*Form and growth habit.*—Perennial, evergreen, shrub; mostly upright and somewhat spreading.

*Branching.*—Freely branching, approximately 4 to 8 lateral branches develop after pinching. Lateral Branches: Approximately 20 cm long and 5 mm in diameter. Internode Length: Approximately 4 cm.

Leaf:

*Shape.*—Ovate. Apex: Rounded. Base: Cordate.

*Leaf size.*—Approximately 11 cm long and 11.5 cm wide.

*Arrangement.*—Alternate, single; symmetrical.

*Margin.*—Undulate with crenulate margins.

*Aspect.*—Undulate.

*Texture/substance.*—Scabrous.

*Coloration.*—Young Foliage Upper side: Near Yellow-Green Group 146B. Under side: Near Yellow-Green Group 146D. Mature Foliage: Upper side: Near Green Group 137A. Under side: Near Green Group 137C.

*Petioles.*—Size: Approximately 4 cm long, 3 mm across. Coloration: Near Yellow-Green Group 144B. Texture: Smooth.

*Hardiness.*—USDA Zone 10 (30° F. to 40° F.).

*Pests/diseases.*—Resistance to known *Hibiscus* diseases had not been observed on plants grown under conditions approximating commercial practices.

Inflorescence:

*Bloom period.*—Typically year-round under subtropical and tropical conditions.

*Flower arrangement.*—Arranged singly at terminal leaf axils; free-flowering with 3 to 4 flower buds and/or open flowers per terminal apex; flowers face upright and slightly outward.

*Flower appearance.*—Ruffled dark pink to light red petals with a darkened eye zone; flowers are open for about two days before closing; flowers persistent.

*Flower diameter.*—Approximately 21 cm.

*Buds* (*just prior to showing color*).—Rate of Opening: Approximately 1 or 2 days, depending on temperature. Shape: Elliptic. Length: Approximately 3 cm. Diameter: Approximately 1.3 cm. Color: Near Yellow-Green Group 144B.

*Fragrance.*—None noted.

*Petals.*—Number/Arrangement: Corolla consists of 5 overlapping petals. Shape: Spatulate with rounded apex. Size: Approximately 10 cm long and 10 cm wide. Margin: Entire, but lightly ruffled. Texture: Smooth. Color Upper Surface: The interior third of the petal starts at near Red Group 53A and fades outward to near Red Group 55B and 55C. Lower Surface: The majority is near Red Group 55C to 55D, eventually fading to White Group N155B at the base of the petal.

*Sepals.*—Number/Arrangement: 5 sepals fused into a star-shaped calyx. Shape: Linear with acuminate apices. Margin: Entire. Color: Near Yellow-Green Group 144A.

*Peduncles.*—Length: Approximately 4 cm. Diameter: Approximately 3 mm. Angle: Upright to about 45 degrees. Strength: Strong, flexible. Color: Near Yellow-Green Group 144B.

Reproductive organs

*Androecium.*—Stamens: Numerous; approximately 50. Stamen Length: Approximately 5 mm. Filament Color: Near Red Group 54B. Anther Length: Approximately 1 mm. Pollen Amount: Abundant. Pollen Color: Yellow-Orange Group 15B.

*Gynoecium.*—Pistil Number: 1. Pistil Length: Approximately 8 cm. Stigma Appearance: 5, rounded. Stigma Diameter: Approximately 2 mm. Stigma Color: Near Orange-Red Group 33A. Style Color: Lower two-thirds near Red Group 53B; fading to near Red Group 55B on the upper third.

*Seed production.*—Seed production has not been observed.

I claim:

1. A new variety of *Hibiscus rosa-sinensis* plant as shown and described.

* * * * *